(12) United States Patent
Faure

(10) Patent No.: US 9,901,396 B2
(45) Date of Patent: *Feb. 27, 2018

(54) PERCUTANEOUS AND LAPAROSCOPIC SURGICAL INSTRUMENT

(71) Applicant: André Faure, Palmetto, FL (US)

(72) Inventor: André Faure, Palmetto, FL (US)

(73) Assignee: Trod Medical, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/244,542

(22) Filed: Aug. 23, 2016

(65) Prior Publication Data

US 2016/0361110 A1 Dec. 15, 2016

Related U.S. Application Data

(63) Continuation of application No. 14/948,630, filed on Nov. 23, 2015, now Pat. No. 9,445,866, which is a
(Continued)

(30) Foreign Application Priority Data

Dec. 8, 2008 (EP) ..................................... 08171007

(51) Int. Cl.
*A61B 18/14* (2006.01)
*A61B 18/12* (2006.01)
(Continued)

(52) U.S. Cl.
CPC ...... *A61B 18/1482* (2013.01); *A61B 18/1206* (2013.01); *A61B 18/1477* (2013.01); *A61B 18/1492* (2013.01); *A61B 90/11* (2016.02); *A61N 1/06* (2013.01); *A61B 2017/3409* (2013.01); *A61B 2017/3411* (2013.01);
(Continued)

(58) Field of Classification Search
CPC ............ A61B 18/1482; A61B 18/1477; A61B 18/148; A61B 2018/1425; A61B 2018/143; A61B 2018/1495; A61B 2018/1435; A61B 2018/00053; A61B 2018/126; A61B 2018/1467; A61B 2018/1475;
(Continued)

(56) References Cited

U.S. PATENT DOCUMENTS 5,507,743 A 4/1996 Edwards et al.
5,837,006 A 11/1998 Ocel et al.
(Continued)

FOREIGN PATENT DOCUMENTS

DE 19713797 A1 10/1997
WO WO 2004/100812 * 11/2004 ............. A61B 18/14
(Continued)

*Primary Examiner* — Thomas Giuliani
(74) *Attorney, Agent, or Firm* — Reinhart Boerner Van Deuren P.C.

(57) ABSTRACT

The present invention relates to a Radiofrequency surgical instrument comprising at least two dry electrodes (3 and 4, or 3 and 5) and a electrode guiding device (6) comprising a main body (7), having a proximal end (73) and a distal end (74), and at least two insertion holes (8 and 81 or 82) guiding said electrodes (3 and 4, or 3 and 5), said insertion holes (8 and 81 or 82) extending through the body (7).

13 Claims, 7 Drawing Sheets

Related U.S. Application Data continuation of application No. 12/992,702, filed as application No. PCT/EP2009/055984 on May 18, 2009, now Pat. No. 9,220,892.

(60) Provisional application No. 61/053,788, filed on May 16, 2008.

(51) Int. Cl.
- *A61N 1/06* (2006.01)
- *A61B 90/11* (2016.01)
- *A61B 17/34* (2006.01)
- *A61B 18/00* (2006.01)

(52) U.S. Cl.
CPC ............... *A61B 2018/00053* (2013.01); *A61B 2018/00107* (2013.01); *A61B 2018/00577* (2013.01); *A61B 2018/00982* (2013.01); *A61B 2018/126* (2013.01); *A61B 2018/143* (2013.01); *A61B 2018/1425* (2013.01); *A61B 2018/1435* (2013.01); *A61B 2018/1467* (2013.01); *A61B 2018/1475* (2013.01)

(58) Field of Classification Search
CPC ............ A61B 90/11; A61B 2017/3409; A61B 2017/3411; A61B 17/3403
USPC .................................. 606/34, 37, 41, 48, 50
See application file for complete search history.

(56) References Cited

U.S. PATENT DOCUMENTS

| | | |
|---|---|---|
| 5,928,229 A | 7/1999 | Gough et al. |
| 9,220,892 B2 | 12/2015 | Faure et al. |
| 9,445,866 B2 | 9/2016 | Faure |
| 2005/0085807 A1 | 4/2005 | Venturelli |
| 2008/0071262 A1 | 3/2008 | Azure |

FOREIGN PATENT DOCUMENTS

| | | |
|---|---|---|
| WO | WO 2004/100812 A1 | 11/2004 |
| WO | WO 2007/144004 A1 | 12/2007 |

\* cited by examiner

PERCUTANEOUS AND LAPAROSCOPIC SURGICAL INSTRUMENT

CROSS-REFERENCE TO RELATED PATENT APPLICATIONS

This patent application is a continuation of U.S. application Ser. No. 14/948,630, filed Nov. 23, 2015, now U.S. Pat. No. 9,445,866, granted Sep. 20, 2016, which is a continuation of U.S. application Ser. No. 12/992,702, filed Nov. 15, 2010, now U.S. Pat. No. 9,220,892, granted Dec. 29, 2015, which is the National Stage of International Application No. PCT/EP2009/055984, filed May 18, 2009, which further claims the benefit of European Application No. 08171007.1, filed Dec. 8, 2008 and U.S. Provisional Application No. 61/053,788, filed May 16, 2008, the entire teachings and disclosure of which are incorporated herein by reference thereto.

FIELD OF THE INVENTION

The present invention relates to a surgical instrument, in particular to a percutaneous and laparoscopic surgical instrument, and relates also to an electrode guiding device for such surgical instruments.

PRIOR ART AND RELATED TECHNICAL BACKGROUND

Radiofrequency (RF) therapy, is a well known non-invasive and outpatient procedure that uses radio waves. Generally, it is used to treat cancer, more particularly for the ablation of tumors from different organs, e.g. breast, colon, lungs, pancreas, prostate, kidney.

In such procedure, electrodes are placed into contact with the tissue to treat and a current, from a RF generator, is applied to the tissue via the electrodes. As the current passes, the tissue between the electrodes heats, a lesion is created, and the corresponding tissue is destroyed.

RF surgical devices are well known. Generally they are monopolar devices.

The device described in U.S. Pat. No. 5,507,743 may be a monopolar or a bipolar device. In the bipolar form of the device, it comprises one straight and one helical (coiled) electrode, the straight electrode being inside the helix formed by the helical one. In U.S. Pat. No. 5,507,743, to increase the size of the lesion created, both electrodes are hollow with a plurality of fluid distribution ports to deliver, into or onto the tissue to be ablated, a conductive fluid, such as chemotherapeutic agent or as an isotonic or hypertonic saline solution.

One of the main disadvantages of such RF surgical devices is that no confinement of the lesion is achieved. Furthermore it is very difficult to predict how wide the lesion created will be.

In WO2004/100812, the bipolar RF device is a three elements device wherein at least two of the elements are "dry" electrodes, i.e. not hollow and not able to deliver a conductive fluid. In the bipolar RF device described, the electrodes may be either both helical (coiled) and parallel one to another, or one helical and one straight. The bipolar RF device works by a cage effect allowing some confinement of the lesion created.

One of the main disadvantages of such bipolar RF surgical devices working with a cage effect, is the imprecise confinement of the lesion created as the positioning of the RF electrodes, to effectively ablate the tissue, may be imprecise.

To ensure optimal performance, the axis of each electrode should be parallel; However, due to the piercing resistance of the skin, the tissue, or the organ to treat, and even if Radiofrequency electrodes are sharp and not deformable, the electrodes are prone to touch, or come close, one to another, leading to a misalignment of the electrodes and a reduced performance of RF devices.

In addition, a controlled widening of the confinement is not possible with such bipolar RF surgical devices.

Aims of the Invention

The present invention aims to provide a percutaneous and laparoscopic surgical device which does not have the drawbacks of the prior art.

Particularly, the invention aims to provide a RF surgical device with enhanced performance.

More particularly, the invention aims to provide a RF surgical device which allow a defined confinement of the lesion created.

The present invention aims also to provide a RF surgical device with stabilised electrodes.

The present invention aims also to provide a device which ensure a dimensional stability of the electrodes of a RF surgical device.

SUMMARY OF THE INVENTION

The present invention relates to a bipolar Radiofrequency surgical instrument comprising at least two dry electrodes, and a electrode guiding device comprising a main body, having a proximal end and a distal end, and at least two insertion holes guiding said electrodes, said insertion holes extending through the body.

The term "dry electrode" should be understood as "solid electrode", solid electrode meaning that the electrode is not hollow and not able to deliver a conductive fluid.

According to particular embodiments, the bipolar Radiofrequency surgical instrument may comprise one or a combination of any of the following characteristics:
  the at least two dry electrodes are helical;
  at least one dry electrode is helical, and at least one dry electrode is straight;
  the at least two dry electrodes are arranged in a concentric manner;
  the shape and the size of the holes correspond to the shape and the size of the corresponding dry electrodes;
  the diameter of the holes do not exceed 10% of the diameter of the electrodes;
  the bipolar Radiofrequency surgical instrument comprises a RF current generator, positioning means, controlling means, location means and imaging means.

The present invention relates also to a device for guiding at least two Radiofrequency electrodes of a bipolar Radiofrequency surgical instrument, said guiding device comprising a main body, having a proximal end and a distal end, and at least two insertion holes guiding said electrodes, said insertion holes extending through the body.

According to particular embodiments, the guiding device may comprise one or a combination of any of the following characteristics:
  the insertion holes are helical and arranged in a concentric manner at the proximal end of said body;
  the body comprises at least one helical insertion hole and one straight insertion holes, said holes being arranged in a concentric manner at the proximal end of said body;

the diameter of the insertion holes do not exceed 10% of the diameter of the electrodes;

the body further comprises at least a supplementary hole at the distal end of the body, said supplementary hole being straight;

the body is circular, and a first series of supplementary holes are arranged, in a tangential manner, at the periphery of said body;

the body further comprises a second series of supplementary holes arranged in a tangential manner in respect to the first series of supplementary holes;

the at least one helical insertion hole is formed by engaging a threaded rod into a circular opening of the body;

the guiding device comprises a fixing part to fasten the guiding device to the head of a laparoscopic surgical instrument or to positioning means of a percutaneous surgical instrument.

The present invention relates also to a kit of parts comprising the guiding device according to the invention, and at least two dry Radiofrequency electrodes.

The present invention relates also to a method to remove a tumor comprising the use of a Radiofrequency surgical instrument according to the invention.

DETAILED DESCRIPTION OF THE INVENTION

Figure 1:
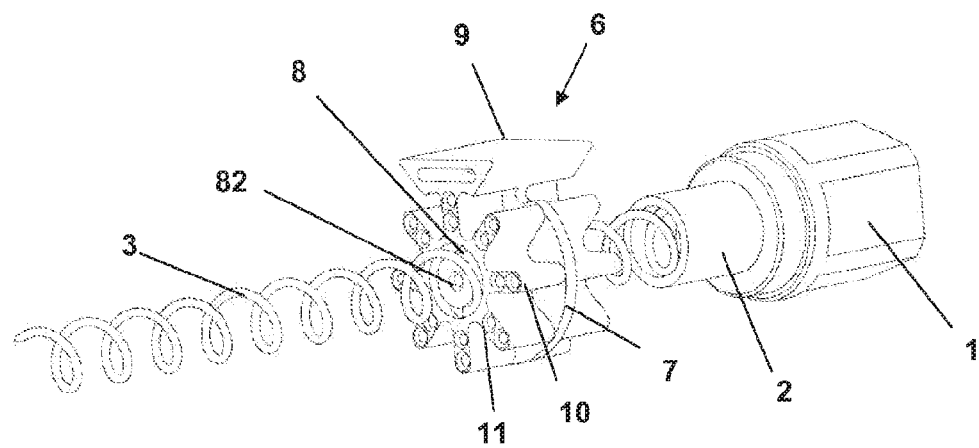
FIG. 1 is a schematic representation of the RF surgical device according to a first preferred embodiment.

The bipolar Radiofrequency surgical instrument according to the present invention comprises at least one helical electrode (FIG. 1), preferably two helical electrodes 3 and 4 (FIG. 2), or an helical electrode 3 and a straight electrode 5 (FIG. 3) and a electrode guiding device 6.

Preferably, the bipolar RF surgical instrument is of the type described in WO2004/100812 which is incorporated herein by reference. The RF surgical device comprise a main body 1, stabilisation means 2 and at least a set of electrodes which can be helical, more preferably two helical electrodes, and even more preferably three helical electrodes. Optionally, it may further comprise a central member 5, which may or may not be a straight electrode, and which is surrounded by the helical electrodes 3 or 4. When the central member 5 is an electrode, it can be used with either a single helical electrode, or with two or more helical electrodes.

The RF electrodes 3, 4 and/or the central member 5 are sharp, not deformable, and rigid electrodes. They are "dry electrodes", i.e. not hollow and not able to deliver a conductive fluid. Preferably, they are made of metal, a biocompatible metal, preferably made of biocompatible stainless steel. It may be for example surgical stainless steel type 304 or type 316.

Preferably, the electrodes and/or the central member 5 are coated with an isolating polymeric compound, for example coated with TFE or polyester. More preferably, they are coated along their length but except on their tip, for example over around one turn for helical electrodes and around 1.5 cm for the central member.

The helical electrodes 3 and 4 may have the same diameter or a diameter different. Preferably, their diameter is between 1 and 2 mm, more preferably around 1.2 mm, or around 2 mm. Preferably, their length is of at least 15 turns, or a length of around 150 cm. The pitch is preferably a right-handed pitch, preferably of between 5 and 20 turns by cm. The helix formed by the helical electrodes 3 or 4 have preferably a diameter comprised between 8 to 24 mm. However, it is possible to adapt the diameter of the helix formed by the helical electrodes 3 or 4 according to the volume of the target tissue to treat.

The helical electrodes 3, 4 are wounded parallel one to the other and have the same pitch. The helix formed by one of the electrode is arranged in a concentric manner in respect to the helix formed by the other, or others, electrodes.

Preferably, the central member 5 have diameter and length corresponding to those of the helical electrode 3 or 4. More preferably, the diameter of the central member 5 is around 1.5 mm.

The central member 5 can be placed at the centre of the helix formed by the helical electrode 3 or 4.

In a preferred embodiment, the helical electrodes 3 and 4, and the central member 5 are fixed in the stabilisation means 2 by any suitable means.

In another preferred embodiment, the helical electrodes 3 and 4 are fixed in the stabilisation means 2 by any suitable means, while the central member 5 is removable.

Preferably, the helical electrodes 3 and 4 are glued in the stabilisation means 2 and are in contact with a connector which can be in electrical contact with a Radiofrequency generator.

As the central member 5 may be removable (FIG. 3), it may comprise at one end a connector which can be in electrical contact with a Radiofrequency generator.

The stabilisation means 2 of the RF surgical instrument have a hollow cylindrical shape, made of a biocompatible polymeric material, for example poly-ether-ether-ketone (PEEK), polycarbonate or polyamide. It further may comprise a channel through which the central member 5 can pass.

Preferably, the stabilisation means 2, comprising the helical electrodes 3 or 4, is disposable. Preferably, the central member 5 is also disposable.

Each electrodes (electrodes 3, 4, and central member 5) can be activated independently one from the other to get a first pole (first electrode) and an second pole (second electrode), "activated" meaning that a current is applied into the electrode.

In on embodiment the first and the second pole are helical electrodes. In another embodiment, the first pole is a helical electrode 3 and the second pole is the central member 5.

Figure 4:
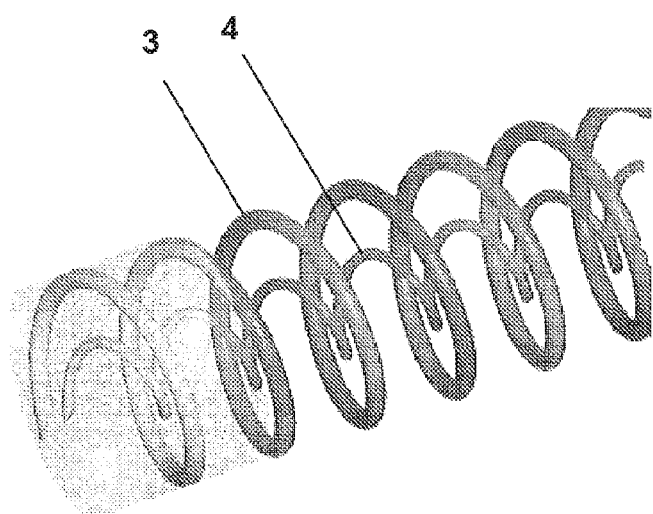
FIG. 4 is a schematic representation of the cage effect whereby the RF surgical device treats the tissue.

When applying a current to at least one electrode of the RF surgical instrument according to the present invention, the surgical instrument works by a cage effect (FIG. 4). The heating created into the tissue goes from the closest electrode to the centre to the furthermost electrode. The tissue, which is in the cage formed by the electrodes, is thus destroyed, while the tissue outside the cage is safe.

The different combination between the type of electrodes (helical and/or straight), and the different diameter of the helix formed by helical electrodes, present the advantage of having a RF surgical instrument which can be easily adapted to the size of the tissue to treat. Furthermore, the use of the central member 5 presents the advantage of having the possibility to treat a smaller tissue volume, for example in combination with a smaller helical electrode (electrode 4). It may further present the advantage of modifying the shape of the treated zone, from a square like shape, in case of use of helical electrodes, to a sharper shape.

The electrode guiding device 6 according to the invention presents the advantage to maintain the dimensional stability of the electrodes by preventing their deformation during the perforation of the skin or the organ. Thus the confinement of the lesion created is precise and the tissue treated is as predicted. The precision of the treatment achieved is below 1 mm. It further enables an easier penetration of the helical electrodes 3 and 4 by making easier the penetration screw like movement.

The electrode guiding device 6 of the RF surgical instrument according to the invention comprises a main body 7 comprising at least two holes 8 and 81 (FIG. 5) or 8 and 82 (FIG. 6), or three holes 8, 81 and 82 (FIG. 7), extending through the body 7.

The body 7 comprises a front side 71, a back side 72, a proximal end 73 and a distal end 74.

The body 7 has any suitable shape, preferably it is substantially round, but may also have, for example, a polygonal or a square shape. It is made of any metal, or of polymeric material. Preferably, it is made of titanium or stainless steel, or of a poly-ether-ether-ketone (PEEK), polycarbonate, or polyamide.

The body 7 comprises at least two holes 8 and 81, or 8 and 82, extending through the body 7 from the front side 71 to the back side 72. Preferably, the holes are arranged at the primal end 73 of the body 7.

Through the body 7, and on the surfaces defined by the front side 71 and the back side 72, the holes 8, 81, and/or 82 have a shape and a diameter enabling the electrodes 3, 4, 5 to go through. Preferably, their shape and diameter correspond substantially to the shape and the diameter of the RF electrodes 3, 4, 5 to guide and which pass thought.

Through the body 7, the hole for a straight electrode is substantially straight, and the hole for a helical electrode is substantially helical or substantially of a corkscrew shape, with either a left-handed or a right-handed pitch depending of the pitch of the helical electrodes. On the surfaces defined by the front side 71 and the back side 72, the hole 82 may be round, square, oval, or octagonal.

The diameter of the holes 8 and 81 is substantially equal, or corresponding, to the diameter of the helix formed by the corresponding electrodes 3 and 4. The size of the opening forming the holes 8 and 81 is substantially equal, or corresponding, to the diameter of the corresponding electrodes 3 and 4, preferably the size of the opening do not exceed 10% of the diameter of the electrodes 3 or 4.

The diameter of the hole 82 is substantially equal, or corresponding, to the diameter of the central member 5, and preferably do not exceed 10% of the diameter of the central member 5.

Figure 5:
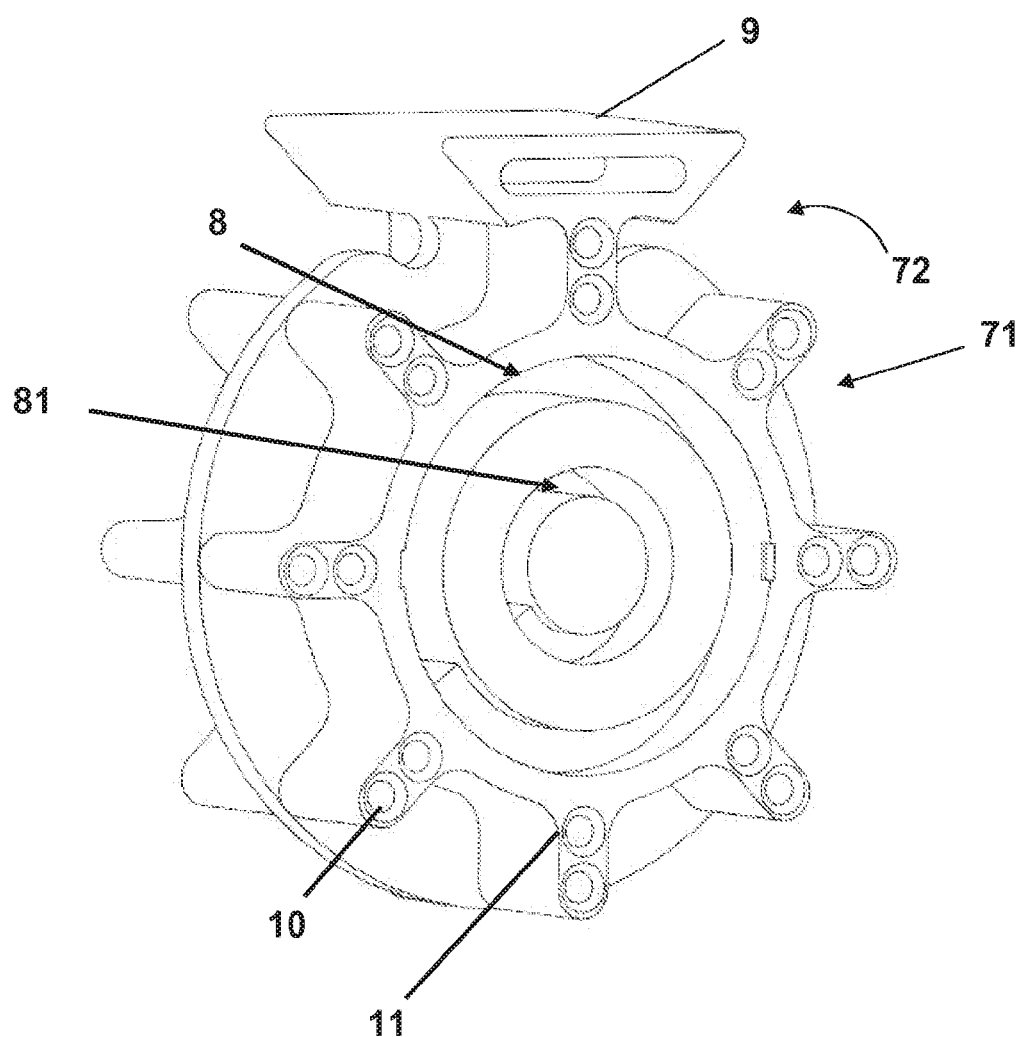
FIG. 5 is a schematic representation of the guiding device according to a first embodiment of the invention.

In a preferred embodiment, the body 7 of the guiding device comprises two helical holes 8 and 81 (FIG. 5).

Figure 6:
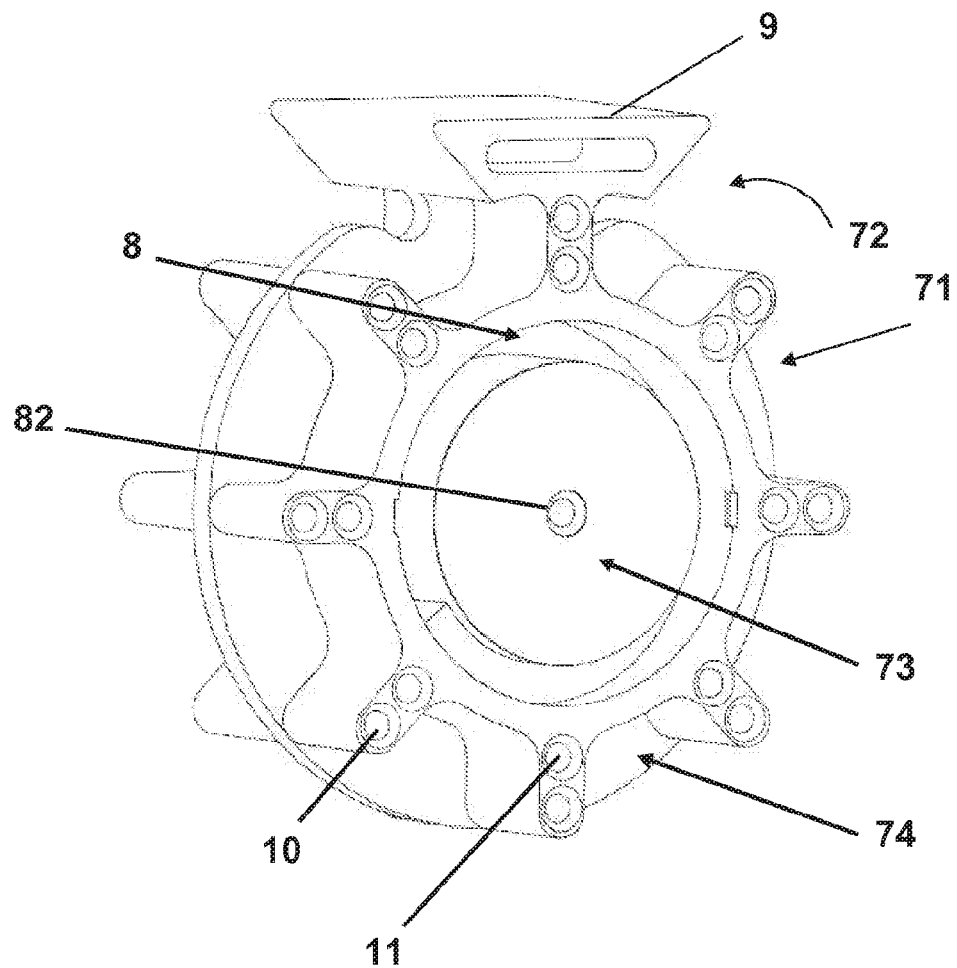
FIG. 6 is a schematic representation of the guiding device according to a second embodiment of the invention.

In another preferred embodiment, the body 7 of the guiding device comprises one helical 8 and one straight hole 82 (FIG. 6).

Figure 7:
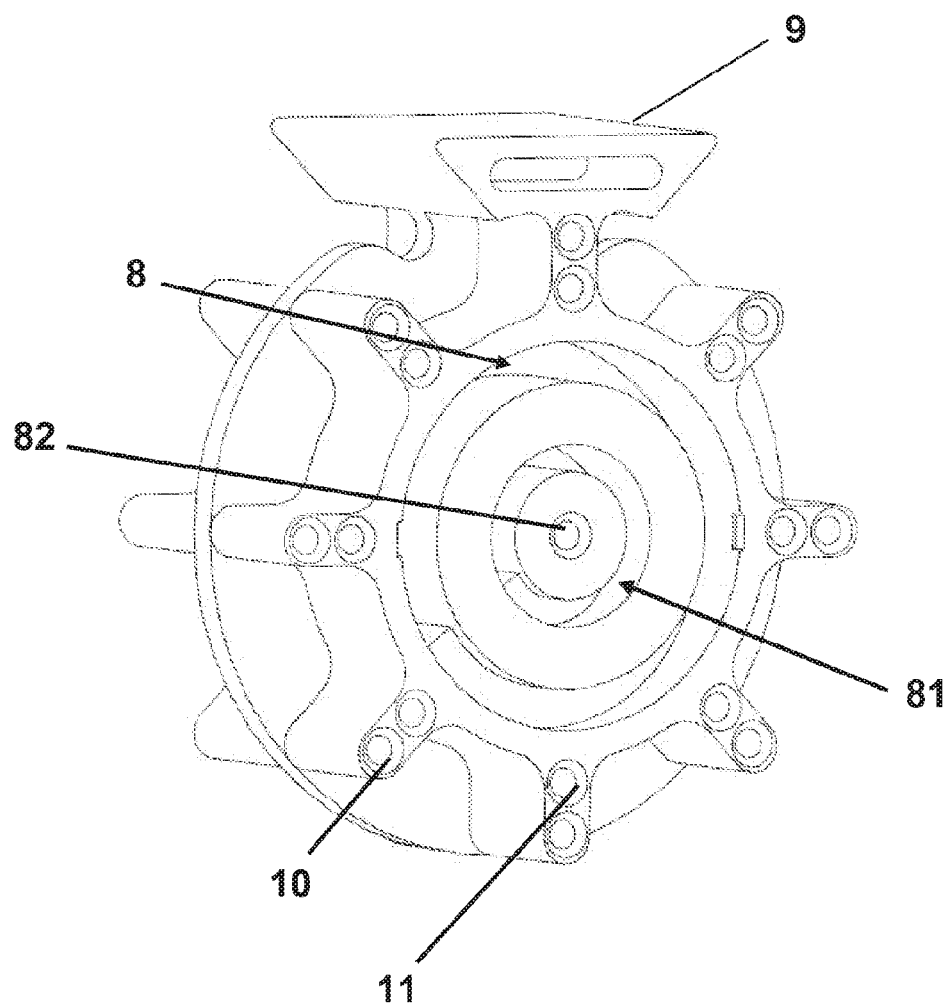
FIG. 7 is a schematic representation of the guiding device according to a third embodiment of the invention.

In another preferred embodiment, the body 7 comprises two helical holes 8, 81 and one straight hole 82 (FIG. 7).

However, the number of holes and their shape are not limited to those disclosed here as examples. The guiding device may comprise as many holes, and as different, as RF electrodes are.

Preferably, the guiding device 6 according to the present invention cooperates with the RF electrodes as described. However, the electrode guiding device may be used with any RF surgical instrument having at least two RF electrodes, straight and/or helical, being either hollow to deliver a conductive fluid, or dry, and having any size and any length. Nevertheless, the electrode guiding device is well suited to devices comprising two helical electrodes wounded parallel one to the other.

Figure 2:
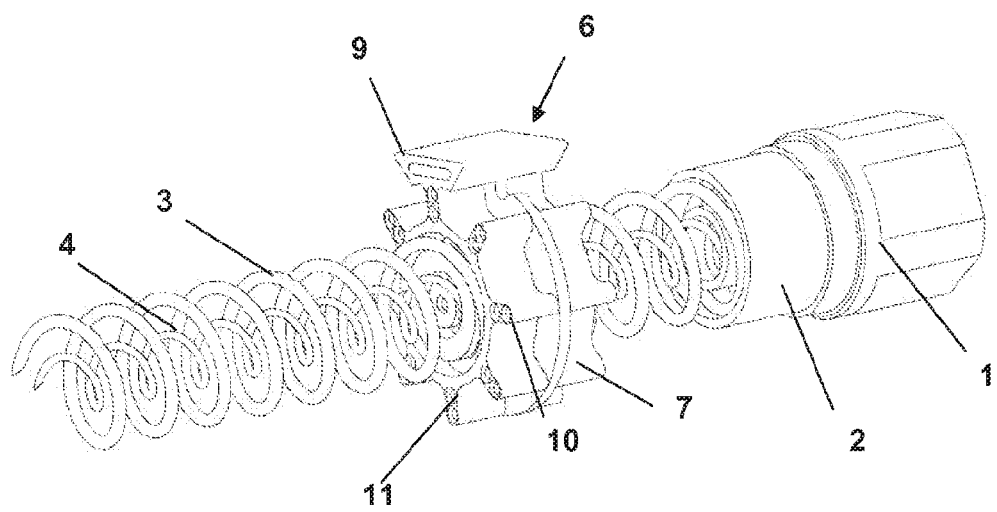
FIG. 2 is a schematic representation of the RF surgical device according to a second preferred embodiment.
Figure 3:
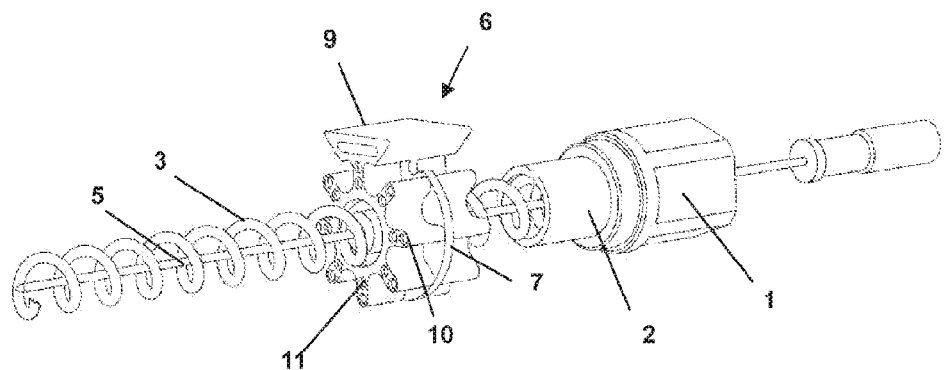
FIG. 3 is a schematic representation of the RF surgical device according to a third preferred embodiment.

The body 7 of the electrode guiding device has an overall size at least higher than the external diameter of the furthermost helical electrode from the centre of said body 7 (electrode 3 in FIGS. 1 to 3). Preferably, the body 7 has a size and a shape enabling his use with a catheter.

Preferably, the body 7 has a overall size of between 8 and 30 mm, a thickness of between 1 and 3 cm. The spacing between two helical holes is around 20 mm.

In another preferred embodiment of the electrode guiding device 6 according to the invention, the body 7 may comprise at least one supplementary hole arranged at the distal end 74 of the body 7. Preferably, the body 7 comprises several straight holes laid in a tangential manner at its periphery. More preferably, the body 7 comprises two series of straight holes 10, 11, laid in a tangential manner at its periphery, the holes 10 of the first series being tangent to the periphery of the body 7, and the holes 11 of the second series being tangent to the holes 10 of the first series of holes (FIGS. 5 to 7).

The supplementary hole 10 and/or 11 guide any other electrode, an anchoring member, or a needle, for example a straight needle, to introduce a conductive fluid or chemotherapeutic agent into the tissue before, during, or after ablation, or a needle biopsy aspiration device or any sensor, for example temperature sensors, or any optical device, or illumination fibres.

In a preferred embodiment, the supplementary holes 10 and/or 11 guide a straight RF electrode. Preferably, the straight RF electrode is of the type of the central member 5.

When the tissue to treat is bigger than the diameter of the biggest helix formed by the outermost helical electrode 3, at least one straight RF electrode can be used, said straight RF electrode being guided precisely where wanted, thanks to the specific arrangement of the supplementary holes 10 and/or 11 into the guiding device 6. To widen the volume of tissue to treat, the RF current is applied either between the helical electrode 3 and the supplementary straight electrode, or between the central member 5 and the supplementary straight electrode.

Optionally, the guiding device further comprises a fixing part 9, to allow the guiding device 6 to be handheld, or to be fixed to a percutaneous surgical instrument or a laparoscopic surgical instrument.

The body 7 of the electrode guiding device may be made either of one piece, or made of the assembly a two elements, one corresponding to the front side 71 and the other corresponding to the back side 72 of the device, the two elements being assembled by any suitable method.

The one piece body 7, or the two elements body 7, may be produced by any suitable method, for example by extrusion, by moulding or by stereolytography.

In a preferred embodiment, the hole 8, 81, 82 and the supplementary hole 10 or 11 are formed during the process to manufacture the body 7. In another embodiment, the hole 8, 81, 82 and the supplementary hole 10 or 11 are drilled, by any suitable means, into the mass of the one piece body 7, or in the two elements corresponding to the front side 71 and the back side 72 of the body 7, the holes being drilled before or after the assembly of the two elements of the body 7.

Figure 8:
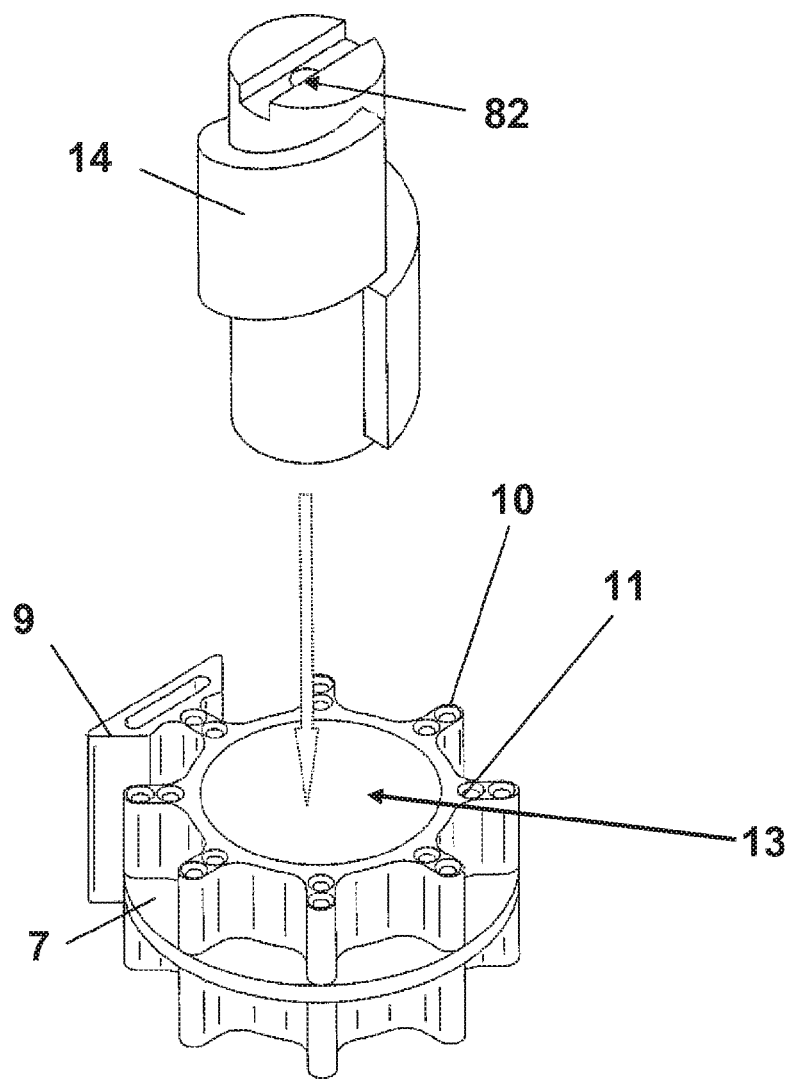
FIG. 8 is a schematic representation of a two pieces embodiment of the guiding device according to the invention.

In another embodiment, the holes 8, 81 or 82 are not drilled but are formed by the assembly of a one piece body 12, or a front side and back side elements assembly, having a circular opening 13, and a threaded rod 14 engaged in said circular opening 13 (FIG. 8). Preferably, the threaded rod 14 is engaged by force in the opening 13 and fixed to the body 7, for example by heat welding or by mean of a biocompatible glue.

Preferably, the threaded rod 14 is made of the same material as the one of the body 7, or as the one of the front side and back side elements, for example, made of PEEK.

The diameter of the opening 13 and the external diameter of the threaded rod 14 are chosen to fit the external diameter of the helical electrode to guide. Furthermore, the length of the threaded rod 14 substantially corresponds to the thickness of the body 7, and its pitch substantially corresponds to the pitch of the helical electrode, in terms of dimension and type of pitch (either left-handed or right-handed thread).

Preferably, the threaded rod 14 further comprises a hole 82, which may be an helical hole or a straight hole. The threaded rod 14 may comprise a helical and a straight hole. The hole 82 may be drill in the threaded rod 14, or may be formed by the engagement a threaded rod in an opening at the centre of the threaded rod 14.

The guiding device 6 may be fastened by any suitable means to a laparoscopic instrument, for example an endoscope, to a positioning head of a percutaneous surgical instrument, or to be held by hand. Preferably, this fastening is achieved by a fixing part 9 of the guiding device 6.

Preferably, the electrode guiding device is disposable.

The RF surgical instrument, and the electrode guiding device, according to the invention, may be parts of a more complex surgical instrument.

In a preferred embodiment, the RF surgical instrument, and the electrode guiding device, according to the invention, may be parts of a laparoscopic surgical instrument, for example an endoscope device. Therefore, the electrode guiding device 6 may be fixed to the head of the endoscope by, for example, a fixing part 9, which may have any suitable shape and size. The front side 71 of the guiding device 6 is place against the organ to treat and the electrodes extend out through the head of the endoscope device, engage, and extend out through, the electrode guiding device 6, and penetrate into the organ in a screw-like movement for helical electrodes, or a straight movement for a straight electrode, as deep as necessary to reach the zone to treat.

The laparoscopic surgical instrument may further comprise a RF current generator, and optionally, spatial location means, optical means, biopsy aspiration means, sensors and/or computer means.

In a preferred embodiment, the RF surgical instrument, and the electrode guiding device, according to the invention, may be parts of a percutaneous surgical instrument. Therefore, the surgical instrument further comprises a RF current generator, and optionally, positioning means, controlling means, location means, imaging means, and computer means.

In percutaneous applications, the front side 71 of the guiding device 6 is place against the skin and is hand-held, for example by the fixing part 9, said fixing part 9 having any suitable shape and size. Then, the electrodes 3, 4 and/or 5 are engaged into the holes of the guiding device, and extend out through the guiding device 6 to penetrate through the skin in a screw-like movement for helical electrodes, or a straight movement for the straight electrode, as deep as necessary to reach the zone to treat. However, this operation may be more automated by using positioning means and controlling means. The RF surgical device may further comprise location means and imaging means.

Figure 9:
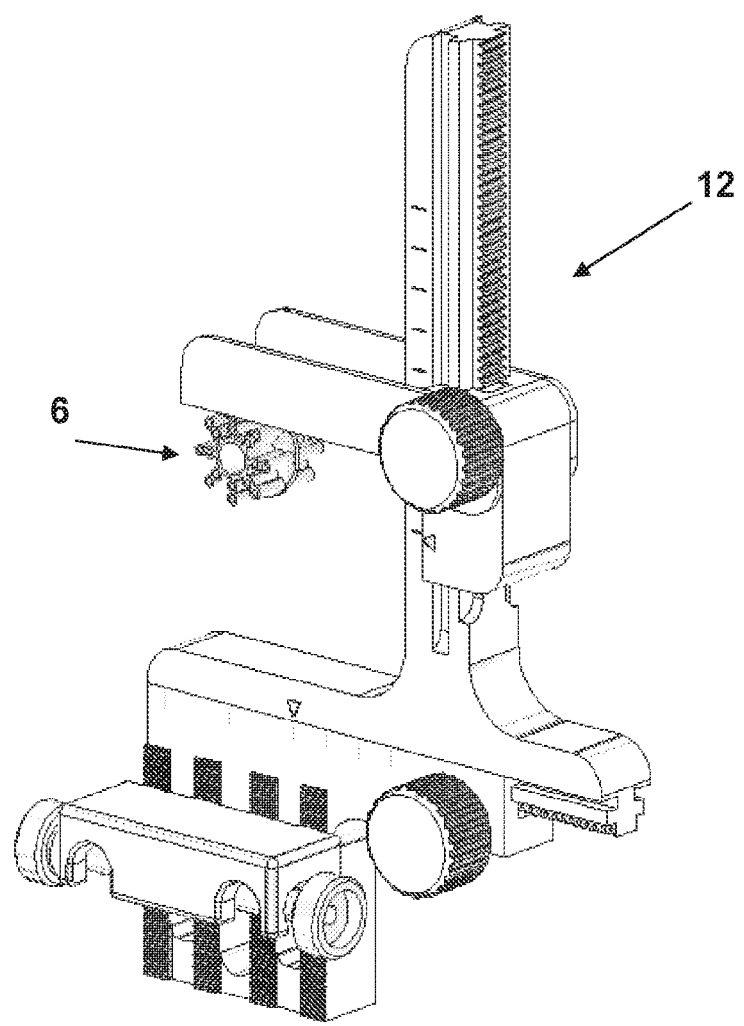
FIG. 9 is a schematic representation of a "X, Y" head of a preferred embodiment of the RF surgical device.

Preferably, the positioning means comprise a "X, Y" head 12 (FIG. 9), or a robot arm, to which the electrode guiding device 6 is fixed, for example by using the fixing part 9 of any suitable shape and size allowing its fastening to the "X, Y" head 12 or robot arm.

The location means, comprising for example a ultrasound probe coupled to imaging means, allow to get the exact position of the tissue to treat and give a reference point to insure the precise positioning of the electrodes using the "X, Y" head 12, before and after the penetration of the electrodes 3, 4, 5. Preferably, the location means are controlled by the computer means.

The front side 71 of the guiding device 6, fastened to the "X, Y" head 12, for example by the fixing part 9, is place against the skin precisely at the point of entry determined by location means, at the level of the tissue to treat, or the area chosen for the treatment. Then, the electrodes 3, 4 and/or 5 extend out through the electrode guiding device 6, and penetrate through the skin as deep as necessary to reach the zone to treat.

The "X, Y" head 12, and/or the movement of the electrodes 3, 4, 5, may be hand-operated, for example by the operator of the surgical instrument, or automatically operated using the controlling means, which may comprise for example a stepper motor which may be controlled by the computer means.

Preferably, in either the laparoscopic or percutaneous embodiments, the treatment of the tissue or the organ may be followed by the location means coupled to the imaging means.

If necessary, to widen the volume of the area to treat, without being obliged to remove the electrodes and to readjust the position with the "X, Y" head 12, one or more straight electrodes may be used. These supplementary electrodes are precisely positioned thanks to the supplementary hole 10 and/or 11 of the guiding device 6. Thus, the area treated is widened while the skin perforation is reduced to a minimum.

The electrode guiding device 6 according to the invention presents the advantage of allowing thus a precise electrodes positioning in respect to the tissue to treat, as it is an alternate solution to the traditional grid used to guide straight electrodes of percutaneous surgical instrument.

It has also the advantage of giving the possibility to widen the treated area by guiding at precise locations supplementary electrodes.

The RF surgical instrument, according to the invention comprising the guiding device 6, presents the advantage of having enhanced performances. It also has the advantage of being adaptable to any size or shape of tumours to treat. It also has the advantage of being minimally invasive.

The RF surgical instrument, according to the invention, may preferably been used to treat prostate, kidney or breast cancer.

The invention claimed is:

1. A surgical assembly, comprising:
a first electrode, wherein the first electrode is rigid and is shaped as a helix, the helix having a first pitch,
a second electrode arranged concentric with the first electrode, and
an electrode guiding device, comprising:
an outer part, an inner part, wherein the inner part is fixed to the outer part, a first through hole, between the outer part and the inner part, and a second through hole through the inner part,
wherein the first through hole is configured for passing the helix therethrough;
wherein the first through hole is representative of a helical pathway having a second pitch corresponding to the first pitch, and
wherein the second through hole is concentric with the first through hole and is configured for passing the second electrode therethrough.

2. The surgical assembly of claim 1, wherein the first through hole allows for advancing the first electrode therethrough by screw-like movement.

3. The surgical assembly of claim 1, wherein the second electrode is straight.

4. The surgical assembly of claim 3, wherein the second through hole is cylindrical.

5. The surgical assembly of claim 1, wherein the second electrode is shaped as a helix having an external diameter smaller than the external diameter of the helix of the first electrode.

6. The surgical assembly of claim 5, wherein the second through hole has a shape substantially corresponding to a shape of the second electrode.

7. The surgical assembly of claim 1, comprising a fixing system allowing for securing the electrode guiding device to a support.

8. The surgical assembly of claim 7, wherein the fixing system is integral with the outer part.

9. The surgical assembly of claim 7, wherein the support is an XY stand.

10. The surgical assembly of claim 1, wherein the outer part comprises a third through hole arranged at a periphery of the first through hole.

11. The surgical assembly of claim 1, wherein the external diameter of the helix is between 8 mm and 24 mm.

12. The surgical assembly of claim 1, wherein the first pitch is between 5 turns per cm and 20 turns per cm.

13. The surgical assembly of claim 1, wherein the helix and the second electrode are allowed to move relative to the outer part and to the inner part.

* * * * *